(12) United States Patent
Takahashi et al.

(10) Patent No.: US 8,124,777 B2
(45) Date of Patent: Feb. 28, 2012

(54) COMPOUND, PHOTOELECTRIC CONVERTER AND PHOTOELECTROCHEMICAL CELL

(75) Inventors: Toshiya Takahashi, Osaka (JP); Akio Tanaka, Hyogo (JP)

(73) Assignee: Sumitomo Chemical Company, Limited, Tokyo (JP)

(*) Notice: Subject to any disclaimer, the term of this patent is extended or adjusted under 35 U.S.C. 154(b) by 811 days.

(21) Appl. No.: 12/067,195

(22) PCT Filed: Sep. 20, 2006

(86) PCT No.: PCT/JP2006/319096
§ 371 (c)(1),
(2), (4) Date: Mar. 18, 2008

(87) PCT Pub. No.: WO2007/034976
PCT Pub. Date: Mar. 29, 2007

(65) Prior Publication Data
US 2010/0180949 A1    Jul. 22, 2010

(30) Foreign Application Priority Data
Sep. 22, 2005 (JP) ................. 2005-275324

(51) Int. Cl.
*C07D 213/22* (2006.01)
(52) U.S. Cl. ........ 546/257; 546/264; 546/261; 546/266; 136/263
(58) Field of Classification Search .......... 136/263; 546/1, 255, 257, 261, 262, 264, 266; 429/111
See application file for complete search history.

(56) References Cited

U.S. PATENT DOCUMENTS
5,463,057 A    10/1995    Graetzel et al.
(Continued)

FOREIGN PATENT DOCUMENTS
JP    2004-296170    * 10/2004
(Continued)

OTHER PUBLICATIONS

"Water photolysis using functional tris(2,2'-bipyridyl)ruthenium (II) complexes" published in Monatshefte fur Chemie (1988), 119(1), pp. 1-15 by Nussbaumer et al. (English abstract provided).*

(Continued)

*Primary Examiner* — Ula C Ruddock
*Assistant Examiner* — Heng Chan
(74) *Attorney, Agent, or Firm* — Sughrue Mion, PLLC (57) ABSTRACT

The present invention provides a compound, a photoelectric converter and a photoelectrochemical cell. The complex compound (I) is obtained by coordinating a ligand represented by the formula (II) and a ligand represented by the formula (III) to a metal atom,

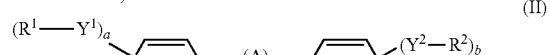

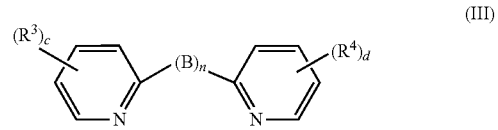

wherein $Y^1$ and $Y^2$ each independently represent a group including an unsaturated hydrocarbon group and an aromatic ring, $R^1$ and $R^2$ each independently represent a protogenic group or a salt thereof, at least one of $R^1$ and $R^2$ is a protogenic group, $R^3$ and $R^4$ each independently represent an aprotogenic group, $R^3$ and $R^4$ may be bound together, A and B each independently represent a group including an element of group 14, 15, or 16 of the Periodic Table, m and n each independently represent an integer of 0 to 2, a, b, c, and d each independently represent an integer of 0 to 2, and $a+b \geq 1$.

5 Claims, 1 Drawing Sheet

U.S. PATENT DOCUMENTS 6,084,176 A * 7/2000 Shiratsuchi et al. .......... 136/263
2009/0000658 A1 1/2009 Zakeeruddin et al.

FOREIGN PATENT DOCUMENTS

JP 2004-296170 A 10/2004

OTHER PUBLICATIONS

Brian O'Regan, A low-cost high efficiency solar cell based on dye-sensitive colloidal Ti02 films, Nature, vol. 353, and volume pp. 737-740 (1991).

* cited by examiner

Fig. 1

COMPOUND, PHOTOELECTRIC CONVERTER AND PHOTOELECTROCHEMICAL CELL

TECHNICAL FIELD

The present invention relates to a compound, a photosensitizing dye including the compound, a photoelectric converter including the dye, and a photoelectrochemical cell including the photoelectric converter such as solar cell.

BACKGROUND ART

In recent years, there has been a demand to reduce the amount of $CO_2$ released into the atmosphere in order to prevent global warming. As an effective means to reduce the amount of $CO_2$, for example, there has been made a proposal to switch over to a solar system in which a photoelectrochemical cell such as silicon-based p-n junction solar cell is provided on the roof of house. However, there has been a problem that single crystal, polycrystal, or amorphous silicon used to fabricate such a silicon-based photoelectrochemical cell is high in cost because there is a need to set up high-temperature and high-vacuum conditions in its manufacturing process.

JP-W No. 7-500630 (Example A) discloses a photoelectrochemical cell which includes a photoelectric converter in which cis-bis(isothiocyanate)bis(2,2'-bipyridyl-4,4'-dicarboxylate)-ruthenium (II) represented by the formula (1) as an easy-to-produce photosensitizing dye is adsorbed on a thin film including titanium oxide fine particles.

(1)

However, there has been a problem that photoelectrochemical cells do not have sufficient photoelectric conversion efficiency at a long wavelength region above 700 nm.

DISCLOSURE OF THE INVENTION

An object of the present invention is to provide a compound used in a photoelectric converter having high photoelectric conversion efficiency even at a long wavelength region of 700 nm or longer.

That is, the invention provides [1] to [20] as follows:

[1] A complex compound (I) obtained by coordinating a ligand represented by the formula (II) and a ligand represented by the formula (III) to a metal atom, wherein $Y^1$ and $Y^2$ each independently represent a group including an unsaturated hydrocarbon group and an aromatic ring, $R^1$ and $R^2$ each independently represent a protogenic group or a salt thereof, at least one of $R^1$ and $R^2$ is a protogenic group, $R^3$ and $R^4$ each independently represent an aprotogenic group, $R^3$ and $R^4$ may be bound together, A and B each independently represent a group including an element of group 14, 15, or 16 of the Periodic Table, m and n each independently represent an integer of 0 to 2, a, b, c, and d each independently represent an integer of 0 to 2, and $a+b \geq 1$.

[2] A complex compound (I) in which a central atom is a metal atom, one of ligands is represented by the formula (II), and another of the ligands is represented by the formula (III), wherein $Y^1$ and $Y^2$ each independently represent a group including an unsaturated hydrocarbon group and an aromatic ring, $R^1$ and $R^2$ each independently represent a protogenic group or a salt thereof, at least one of $R^1$ and $R^2$ is a protogenic group, $R^3$ and $R^4$ each independently represent a hydrogen atom or an aprotogenic group, $R^3$ and $R^4$ may be bound together, A and B each independently represent a group including an element of group 14, 15, or 16 of the Periodic Table, m and n each independently represent, an integer of 0 to 2, a b, c, and d each independently represent an integer of 0 to 2, and $a+b \geq 1$.

[3] The complex compound (I) according to [1] or [2], wherein $R^1$ and $R^2$ is each at least one protogenic group selected from the group consisting of phenolic hydroxyl group, carboxyl group, sulfonic acid group, squaric acid group, phosphoric acid group, boric acid group, and silicic acid group or a salt thereof.

[4] The complex compound (I) according to any one of [1] to [3], wherein $R^1$ and $R^2$ are a carboxyl group or a salt thereof.

[5] The complex compound (I) according to any one of [1] to [4], wherein the salt of the carboxyl group is a quaternary salt thereof.

[6] The complex compound (I) according to any one of [1] to [5], wherein $R^3$ and $R^4$ are each a hydrogen atom or at least one group selected from the group consisting of $C_1$-$C_{20}$ alkyl group, $C_1$-$C_{20}$ alkoxy group, $C_2$-$C_{20}$ alkoxyalkyl group, $C_6$-$C_{20}$ aryloxy group, $C_7$-$C_{20}$ arylalkyloxy group, $C_7$-$C_{20}$ aryloxyalkyl group, $C_1$-$C_{20}$ alkylthio group, $C_2$-$C_{20}$ alkylthioalkyl group, $C_6$-$C_{20}$ arylthio group, $C_7$-$C_{20}$ arylalkylthio group, $C_7$-$C_{20}$ arylthioalkyl group, $C_1$-$C_{20}$ alkylsulfonyl group, $C_6$-$C_{20}$ arylsulfonyl group, and amino group which is 2-substituted by $C_1$-$C_{20}$ alkyl group or $C_6$-$C_{20}$ aryl group.

[7] The complex compound (I) according to any one of [1] to [6], wherein $R^3$ and $R^4$ are each a hydrogen atom or a $C_1$-$C_{20}$ alkyl group.

[8] The complex compound (I) according to any one of [1] to [6], wherein $R^3$ and $R^4$ are each a $C_1$-$C_{20}$ alkoxy group.

[9] The complex compound (I) according to any one of [1] to [8], wherein $Y^1$ and $Y^2$ are each a group represented by the formula (IV), (IV)

Ar represents an aromatic group and p represents an integer of 1 to 3.

[10] The complex compound (I) according to [9], wherein $R^1$ and $R^2$ each bind to Ar.

[11] The complex compound (I) according to [10], wherein Ar represents thiophene and p=1.

[12] The complex compound (I) according to any one of [1] to [11], wherein -(A)$_m$- and —(B)$_n$— are each independently at least one group selected from the group consisting of —S—, —O—, —SO—, —SO$_2$—, —PR$^5$—, —NR$^5$—, —Si(R$^5$)(R$^6$)—, and —Se—, and $R^5$ and $R^6$ each independently represent a hydrogen atom, $C_1$-$C_{20}$ alkyl group, or $C_6$-$C_{20}$ aryl group.

[13] The complex compound (I) according to any one of [1] to [12], wherein -(A)$_m$- and/or —(B)$_n$— are —S—.

[14] The complex compound (I) according to any one of [1] to [13], wherein a+b=2 and c+d=2.

[15] The complex compound (I) according to any one of [1] to [14], wherein m=0 and n=1.

[16] The complex compound (I) according to any one of [1] to [14], wherein m=0 and n=0.

[17] The complex compound (I) according to any one of [1] to [16], wherein $R^1$—$Y^1$— and $R^2$—$Y^2$— are each a group represented by the formula (V'), $R^3$ and $R^4$ are each a hydrogen atom or at least one group selected from the group consisting of $C_1$-$C_{20}$ alkyl group, $C_1$-$C_{20}$ alkoxy group, $C_2$-$C_{20}$ alkoxyalkyl group, $C_6$-$C_{20}$ aryloxy group, $C_7$-$C_{20}$ arylalkyloxy group, and $C_7$-$C_{20}$ aryloxyalkyl group, and B is —S—.

(V')

[18] The complex compound (I) according to any one of [1] to [17], wherein the metal atom is Fe, Ru, or Os.

[19] A photosensitizing dye comprising the complex compound (I) according to any one of [1] to [18].

[20] A photoelectric converter comprising a semiconductor fine-particle layer on which the photosensitizing dye according to [19] is adsorbed.

[21] A photoelectrochemical cell comprising the photoelectric converter according to [20], a charge transport layer, and a counter electrode.

EXPLANATION OF REFERENCES 1 substrate
2 conductive layer
3 semiconductor particle layer
4 photosensitizing dye
5 electrolyte
6 conductive layer
7 substrate
8 conductive substrate
9 counter electrode
10 sealer

MODE OF CARRYING OUT THE INVENTION

The present invention will be described in detail below.

A complex compound (I) of the invention is obtained by coordinating ligands represented by the formulas (II) and (III) to a metal atom such as Fe, Ru, or Os, preferably Ru.

Furthermore, the complex compound (I) of the invention is a compound in which a central atom is a metal atom such as Fe, Ru, or Os, preferably Ru, one of ligands is represented by the formula (II), and another of the ligands is represented by the formula (III).

In the formula (II), $R^1$ and $R^2$ each independently represent a protogenic group or a salt thereof, and at least one of $R^1$ and $R^2$ is a protogenic group.

Incidentally, the term protogenic group refers to a group which includes active hydrogen (hydrogen which forms hydrocarbon by reaction with a Grignard reagent); examples of the protogenic group include phenolic hydroxyl group, carboxyl group, sulfonic acid group, squaric acid group, phosphoric acid group, boric acid group, and silicic acid group. Among them, the protogenic group is preferably phenolic hydroxyl group, carboxyl group, and sulfonic acid group, more preferably carboxyl group from the viewpoint of easy production.

At least one of $R^1$ and $R^2$ may be a salt. As the salt, a salt of an organic base is used. Examples of the salt include quaternary salt such as traalkylammonium salt, imidazolium salt, and pyridinium salt.

$Y^1$ and $Y^2$ are each a group including an unsaturated hydrocarbon group (an olefinic hydrocarbon group or an acetylene hydrocarbon group) and an aromatic ring, preferably a group which is conjugated with the pyridine ring in the formula (II).

It is preferable that $Y^1$ is the same as $Y^2$ from the viewpoint of easy production.

Examples of $Y^1$ and $Y^2$ include the group represented by the formula (IV) or (IV'), preferably the group represented by the formula (IV).

(IV)

(IV')

In the formula (IV) or (IV'), Ar represents an aromatic group and p represents an integer of 1 to 3.

Examples of Ar include the following; asterisks (*) in the following examples represent binding sites. Ar is preferably a group represented by the formula (A-4).

(A-1) phenyl (A-2) naphthyl (A-3) pyridyl (A-4) thienyl (A-5) furyl (A-6) pyrrolyl (A-7) imidazolyl (A-8) thiazolyl (A-9) oxazolyl (A-10) 1,2,4-triazolyl (A-10') 1,2,3-triazolyl (A-11) 1,3,4-thiadiazolyl (A-12) pyrazolyl (A-13) isoxazolyl (A-14) isothiazolyl (A-15) pyridazinyl (A-16) pyrimidinyl (A-17) pyrazinyl (A-18) indolyl (A-19) benzofuranyl (A-20) benzothienyl (A-21) quinolinyl (A-22) isoquinolinyl In the formula (IV) or (IV'), p represents an integer of 1 to 3, preferably 1.

When p is 2 or 3, a constitutional isomer of either an E structure or a Z structure may be formed; a mixture of an E structure and a Z structure may be used.

In the group represented by the formula (IV) or (IV'), Ar may be bound to $R^1$ or $R^2$, or may be bound to the pyridine ring; preferably, Ar is bound to $R^1$ or $R^2$.

The asterisks (*) each represent the binding site in which Ar is bound to $R^1$ or $R^2$. With Ar including hetero atoms, Ar is usually bound to $R^1$ or $R^2$ at the site near the hetero atom (a sulfur atom or oxygen atom is given priority over a nitrogen atom) or at the site in which the hetero atoms are present at its both sides.

$Y^1$ and $Y^2$ are each preferably the group represented by the formula (IV). It is preferable that Ar in the group represented by the formula (IV) is preferably a group bound to $R^1$ or $R^2$. It is more preferable that Ar represent thiophene and p is 1.

In the formula (II), a and b each independently represent an integer of 0 to 2, and satisfy $a+b \geqq 1$. The formula (II) includes at least one protogenic group. It is preferable that a and b satisfy $a=b=1$.

In the formula (III), $R^3$ and $R^4$ each independently represent a hydrogen atom or an aprotogenic group. Incidentally, the term aprotogenic group refers to a group which includes no active hydrogen (hydrogen which forms hydrocarbon by reaction with a Grignard reagent; specific examples of the aprotogenic group include alkyl group, alkoxy group, alkoxyalkyl group, aryloxy group, arylalkyloxy group, aryloxyalkyl group, alkylthio group, alkylthioalkyl group, arylthio group, arylalkylthio group, arylthioalkyl group, alkylsulfonyl group, arylsulfonyl group, and amino group 2-substituted with alkyl groups or aryl groups.

In this case, the alkyl group has a carbon number of from 1 to 20, preferably from 2 to 12. Examples of the alkyl group include: straight-chain alkyl groups such as methyl group, ethyl group, n-propyl group, n-butyl group, n-hexyl group, n-pentyl group, n-octyl group, and n-nonyl group; branched-chain alkyl groups such as i-propyl group, t-butyl group, and 2-ethyl-hexyl group; and alicyclic alkyl groups such as cyclopropyl group and cyclohexyl group.

The aryl group has a carbon number of from 6 to 20. Examples of the aryl group include aromatic groups such as phenyl group, naphthyl group, and benzyl group. The carbon atoms included in the alkyl group or aryl group may be substituted with oxygen atoms, sulfur atoms, or nitrogen atoms.

Examples of the amino group 2-substituted with alkyl groups or aryl groups include: dialkylamino groups including a straight-chain or branched-chain alkyl group such as dimethylamino group, diethylamino group, dipropylamino group, methylethylamino group, methylhexylamino group, and methyloctylamino group; aromatic amino groups such as phenylamino group, naphthylamino group, and benzylamino group; and diaromatic amino groups such as diphenylamino group, dinaphthylamino group, and dibenzylamino group.

$R^3$ and $R^4$ may be bound together. And further, when $c=2$ (or $d=2$), for example, $R^3$'s (or $R^4$'s) may be bound together.

In the formula (III), c and d each independently represent an integer of 0 to 2.

In the formula (III), c and d each independently represent an integer of 0 to 2, and satisfy $c+d \geqq 1$. That is, the formula (III) include at least one aprotogenic group. It is preferable c and d satisfy $c+d=1$. Among these it is more preferable that a, b, c and d satisfy $a+b=2$ and $c+d=2$.

$R^3$ and $R^4$ are each preferably a hydrogen atom, $C_1$-$C_{20}$ alkyl group, $C_1$-$C_{20}$ alkoxy group, or $C_2$-$C_{20}$ alkoxyalkyl group, more preferably a hydrogen atom, $C_1$-$C_{20}$ alkyl group, or $C_1$-$C_{20}$ alkoxy group.

In the formulas (II) and (III), A and B each independently represent a group including an element of the 14, 15, or 16 group of the Periodic Table.

In the formulas (II) and (III), m and n each independently represent an integer of 0 to 2. It is preferable that m and n satisfy $m=0$ and $n=1$, or $m=0$ and $n=0$. It is more preferable that m and n satisfy $m=0$ and $n=1$.

Examples of -(A)m- and —(B)n- include —S—, —O—, —$SO_2$—, —P($R^5$)—, —N($R^5$)—, —Si ($R^5$)($R^6$)—, and —Se—, preferably —S—. Incidentally, $R^5$ and $R^6$ each independently represent a hydrogen atom, $C_1$-$C_{20}$ alkyl group, or $C_6$-$C_{20}$ aryl group. Examples of the $C_1$-$C_{20}$ alkyl group include: straight-chain alkyl groups such as methyl group, ethyl group, n-propyl group, n-butyl group, n-hexyl group, n-pentyl group, n-octyl group, and n-nonyl group; branched-chain alkyl groups such as i-propyl group, t-butyl group, and 2-ethyl-hexyl group; and alicyclic alkyl groups such as cyclopropyl group and cyclohexyl group. Examples of the $C_6$-$C_{20}$ aryl group include aromatic groups such as phenyl group, naphthyl group, and benzyl group.

For example, a compound (II) may be produced by a method in which a 2-halogen-substituted pyridine derivative including $Y^1$ and $Y^2$ is react with a suitable phosphine ligand in the presence of a Ni catalyst or a Pd catalyst to induce couple reaction at the 2-position of the pyridine derivative to obtain a compound ($m=0$) (which is represented by the upper formula of the formula (2) below).

In the case A (or B) is a sulfur atom, it is reacted with sulfide soda in an organic solvent to obtain a compound cross-linked with the sulfur atoms ($m=1$ or 2, hereinafter referred to as "S cross-linker") (which is represented by the lower formula of the formula (2) below).

In the case A (or B) is SO or $SO_2$, S cross-linker is oxidized by an m-chloroperbenzoic acid or the like to obtain a compound.

In the method for producing the compound (II), a step may be performed at which after introducing a protecting group such as ester (e.g., a methyl ester, ethyl ester, propyl ester, or butyl ester) into $R^1$ and $R^2$, they are coupled, and then the protecting group is removed.

(2)

(X's each independently represent a chlorine atom, bromine atom, or iodine atom.)

The 2-halogen-substituted pyridine derivative including $Y^1$ and $Y^2$ may be prepared by incorporating an olefin through the Wittig reaction, the Suzuki reaction, or the like; for example, the derivative may be prepared by the following reaction.

A compound (III) may be produced using the same method as the compound (II) except that as the 2-halogen-substituted pyridine derivative, a derivative is used in which $Y^1$ and $Y^2$ are not included, -(A)m- is replaced with —(B)n-, and aprotogenic groups as $R^3$ and $R^4$ are bound thereto instead of $R^1$ and $R^2$.

As the compounds (II) and (III), commercially available dipyridyl compounds may be used.

Examples of the compound (II) include compounds represented by the following formula and shown in Table 1.

TABLE 1

(II-1~II-50)

| Compound | position | —(Y1—R1)a R¹ | position | —(Y2—R2)b R² | Y1 = Y2 Y1, Y2 | Ar | p | A | m | a | b |
|---|---|---|---|---|---|---|---|---|---|---|---|
| II-1 | 4 | —COOH | 4' | —COOH | —(CH=CH)— | A-1 | 1 | — | 0 | 1 | 1 |
| II-2 | 4 | —COOH | 4' | —COOH | —(CH=CH)— | A-2 | 1 | — | 0 | 1 | 1 |
| II-3 | 4 | —COOH | 4' | —COOH | —(CH=CH)— | A-3 | 1 | — | 0 | 1 | 1 |
| II-4 | 4 | —COOH | 4' | —COOH | —(CH=CH)— | A-4 | 1 | — | 0 | 1 | 1 |
| II-5 | 4 | —COOH | 4' | —COOH | —(CH=CH)— | A-5 | 1 | — | 0 | 1 | 1 |
| II-6 | 4 | —COOH | 4' | —COOH | —(CH=CH)— | A-6 | 1 | — | 0 | 1 | 1 |
| II-7 | 4 | —COOH | 4' | —COOH | —(CH=CH)— | A-7 | 1 | — | 0 | 1 | 1 |
| II-8 | 4 | —COOH | 4' | —COOH | —(CH=CH)— | A-8 | 1 | — | 0 | 1 | 1 |
| II-9 | 4 | —COOH | 4' | —COOH | —(CH=CH)— | A-9 | 1 | — | 0 | 1 | 1 |
| II-10 | 4 | —COOH | 4' | —COOH | —(CH=CH)— | A-10 | 1 | — | 0 | 1 | 1 |
| II-11 | 4 | —COOH | 4' | —COOH | —(CH=CH)— | A-11 | 1 | — | 0 | 1 | 1 |
| II-12 | 4 | —COOH | 4' | —COOH | —(CH=CH)— | A-12 | 1 | — | 0 | 1 | 1 |
| II-13 | 4 | —COOH | 4' | —COOH | —(CH=CH)— | A-13 | 1 | — | 0 | 1 | 1 |
| II-14 | 4 | —COOH | 4' | —COOH | —(CH=CH)— | A-14 | 1 | — | 0 | 1 | 1 |
| II-15 | 4 | —COOH | 4' | —COOH | —(CH=CH)— | A-15 | 1 | — | 0 | 1 | 1 |
| II-16 | 4 | —COOH | 4' | —COOH | —(CH=CH)— | A-16 | 1 | — | 0 | 1 | 1 |
| II-17 | 4 | —COOH | 4' | —COOH | —(CH=CH)— | A-17 | 1 | — | 0 | 1 | 1 |
| II-18 | 4 | —COOH | 4' | —COOH | —(CH=CH)— | A-18 | 1 | — | 0 | 1 | 1 |
| II-19 | 4 | —COOH | 4' | —COOH | —(CH=CH)— | A-19 | 1 | — | 0 | 1 | 1 |
| II-20 | 4 | —COOH | 4' | —COOH | —(CH=CH)— | A-20 | 1 | — | 0 | 1 | 1 |
| II-21 | 4 | —COOH | 4' | —COOH | —(CH=CH)— | A-21 | 1 | — | 0 | 1 | 1 |
| II-22 | 4 | —COOH | 4' | —COOH | —(CH=CH)— | A-22 | 1 | — | 0 | 1 | 1 |
| II-23 | 4 | —COOH | 4' | —COOH | —(CH=CH)— | A-4 | 1 | —S— | 1 | 1 | 1 |
| II-24 | 4 | —COOH | 4' | —COOH | —(CH=CH)— | A-4 | 1 | —SO2— | 1 | 1 | 1 |
| II-25 | 4 | —COOH | 4' | —COOH | —(CH=CH)— | A-4 | 1 | —Se— | 1 | 1 | 1 |
| II-26 | 4 | —COOH | 4' | —COOH | —(CH=CH)— | A-4 | 1 | —O— | 1 | 1 | 1 |
| II-27 | 4 | —COOH | 4' | —COOH | —(CH=CH)— | A-4 | 1 | —NH— | 1 | 1 | 1 |
| II-28 | 4 | —COOH | 4' | —COOH | —(CH=CH)— | A-4 | 1 | —NC2H5— | 1 | 1 | 1 |
| II-29 | 4 | —COOH | 4' | —COOH | —(CH=CH)— | A-4 | 1 | —PCH3— | 1 | 1 | 1 |
| II-30 | 4 | —COOH | 4' | —COOH | —(CH=CH)— | A-4 | 1 | —Si(CH3)2— | 1 | 1 | 1 |
| II-32 | 4 | —COOH | 4' | —COOH | —(C≡C)— | A-4 | 1 | — | 0 | 1 | 1 |
| II-33 | 4 | —SO3H | 4' | —SO3H | —(CH=CH)— | A-4 | 1 | — | 0 | 1 | 1 |
| II-34 | 4 | —SO3H | 4' | —SO3H | —(CH=CH)— | A-4 | 1 | —S— | 1 | 1 | 1 |
| II-35 | 4 | —SO3H | 4' | —SO3H | —(CH=CH)— | A-4 | 1 | —SO2— | 1 | 1 | 1 |
| II-36 | 4 | —SO3H | 4' | —SO3H | —(CH=CH)— | A-4 | 1 | —Se— | 1 | 1 | 1 |

TABLE 1-continued (II-1~II-50)

(R¹—Y¹)ₐ at 4, (Y²—R²)ᵦ at 4', with (A)ₘ linker between two pyridine rings

| Compound | —(Y1—R1)a position | R¹ | —(Y2—R2)b position | R² | Y1, Y2 | Ar | p | A | m | a | b |
|---|---|---|---|---|---|---|---|---|---|---|---|
| II-37 | 4 | —SO3H | 4' | —SO3H | —(CH=CH)— | A-4 | 1 | —O— | 1 | 1 | 1 |
| II-38 | 4 | —SO3H | 4' | —SO3H | —(CH=CH)— | A-4 | 1 | —NH— | 1 | 1 | 1 |
| II-39 | 4 | —SO3H | 4' | —SO3H | —(CH=CH)— | A-4 | 1 | —NC2H5— | 1 | 1 | 1 |
| II-40 | 4 | —SO3H | 4' | —SO3H | —(CH=CH)— | A-4 | 1 | —PCH3— | 1 | 1 | 1 |
| II-41 | 4 | —SO3H | 4' | —SO3H | —(CH=CH)— | A-4 | 1 | —Si(CH3)2— | 1 | 1 | 1 |
| II-42 | 4 | —PO3H2 | 4' | —PO3H2 | —(CH=CH)— | A-4 | 1 | — | 0 | 1 | 1 |
| II-43 | 4 | —PO3H2 | 4' | —PO3H2 | —(CH=CH)— | A-4 | 1 | —S— | 1 | 1 | 1 |
| II-44 | 4 | —PO3H2 | 4' | —PO3H2 | —(CH=CH)— | A-4 | 1 | —SO2— | 1 | 1 | 1 |
| II-45 | 4 | —PO3H2 | 4' | —PO3H2 | —(CH=CH)— | A-4 | 1 | —Se— | 1 | 1 | 1 |
| II-46 | 4 | —PO3H2 | 4' | —PO3H2 | —(CH=CH)— | A-4 | 1 | —O— | 1 | 1 | 1 |
| II-47 | 4 | —COOH | 4' | —COOH | —(C≡C)— | A-4 | 1 | —NH— | 1 | 1 | 1 |
| II-48 | 4 | —COOH | 4' | —COOH | —(C≡C)— | A-4 | 1 | —NC2H5— | 1 | 1 | 1 |
| II-49 | 4 | —COOH | 4' | —COOH | —(C≡C)— | A-4 | 1 | —PCH3— | 1 | 1 | 1 |
| II-50 | 4 | —COOH | 4' | —COOH | —(C≡C)— | A-4 | 1 | —Si(CH3)2— | 1 | 1 | 1 |

(In each pyridine ring, a nitrogen atom is at the 1-position and a carbon atom bound to A is at the 2-position. The number of Ar corresponds with that exemplified above.)

Examples of the compound (III) include compounds represented by the following formula and shown in Table 2.

TABLE 2

(III-1~III-62)

$(R^3)_c$ at 4, $(R^4)_d$ at 4', with $(B)_n$ linker between two pyridine rings

| Compound | R³ position | R³ group | R⁴ position | R⁴ group | S | n | c | d |
|---|---|---|---|---|---|---|---|---|
| III-1 | 4 | H | 4' | H | —S— | 1 | 1 | 1 |
| III-2 | 4 | —CH3 | 4' | —CH3 | —S— | 1 | 1 | 1 |
| III-3 | 4 | —CH2CH3 | 4' | —CH2CH3 | —S— | 1 | 1 | 1 |
| III-4 | 4 | -n-Pr | 4' | -n-Pr | —S— | 1 | 1 | 1 |
| III-5 | 4 | -i-Pr | 4' | -i-Pr | —S— | 1 | 1 | 1 |
| III-6 | 4 | -n-Bu | 4' | -n-Bu | —S— | 1 | 1 | 1 |
| III-7 | 4 | -t-Bu | 4' | -t-Bu | —S— | 1 | 1 | 1 |
| III-8 | 4 | —C10H21 | 4' | —C10H21 | —S— | 1 | 1 | 1 |
| III-9 | 4 | —OCH3 | 4' | —OCH3 | —S— | 1 | 1 | 1 |
| III-10 | 4 | —OCH2CH3 | 4' | —OCH2CH3 | —S— | 1 | 1 | 1 |
| III-11 | 5 | —OCH3 | 5' | —OCH3 | —S— | 1 | 1 | 1 |
| III-12 | 4 | —CH(—OCH2CH2O—) | 4' | —CH(—OCH2CH2O—) | —S— | 1 | 1 | 1 |
| III-13 | 4 | —OiPr | 4' | —OiPr | —S— | 1 | 1 | 1 |
| III-14 | 4 | —OH | 4' | —OH | —S— | 1 | 1 | 1 |
| III-15 | 4 | —N(CH3)2 | 4' | —N(CH3)2 | —S— | 1 | 1 | 1 |
| III-16 | 4 | —N(CH3)(C4H9) | 4' | —N(CH3)(C4H9) | —S— | 1 | 1 | 1 |
| III-17 | 4 | —N(C4H9)2 | 4' | —N(C4H9)2 | —S— | 1 | 1 | 1 |
| III-18 | 4 | —N(CH3)(C4H9) | 4' | —N(CH3)(C4H9) | —S— | 1 | 1 | 1 |
| III-19 | 3 | —CH3 | 3' | —CH3 | —S— | 1 | 1 | 1 |
| III-20 | 4 | —CH3 | 4' | —CH3 | —O— | 1 | 1 | 1 |
| III-21 | 4 | —CH2CH3 | 4' | —CH2CH3 | —O— | 1 | 1 | 1 |
| III-22 | 4 | -t-Bu | 4' | -t-Bu | —O— | 1 | 1 | 1 |
| III-23 | 4 | —C10H21 | 4' | —C10H21 | —O— | 1 | 1 | 1 |
| III-24 | 4 | —OCH2CH3 | 4' | —OCH2CH3 | —O— | 1 | 1 | 1 |
| III-25 | 4 | —N(CH3)2 | 4' | —N(CH3)2 | —O— | 1 | 1 | 1 |
| III-26 | 4 | —N(C4H9)2 | 4' | —N(C4H9)2 | —O— | 1 | 1 | 1 |
| III-27 | 4 | —CH3 | 4' | —CH3 | —Se— | 1 | 1 | 1 |
| III-28 | 4 | —CH2CH3 | 4' | —CH2CH3 | —Se— | 1 | 1 | 1 |
| III-29 | 4 | -t-Bu | 4' | -t-Bu | —Se— | 1 | 1 | 1 |
| III-30 | 4 | —C10H21 | 4' | —C10H21 | —Se— | 1 | 1 | 1 |
| III-31 | 4 | —OCH2CH3 | 4' | —OCH2CH3 | —Se— | 1 | 1 | 1 |
| III-32 | 4 | —N(CH3)2 | 4' | —N(CH3)2 | —Se— | 1 | 1 | 1 |
| III-33 | 4 | —N(C4H9)2 | 4' | —N(C4H9)2 | —Se— | 1 | 1 | 1 |

TABLE 2-continued (III-1~III-62)

| Compound | R³ position | R³ group | R⁴ position | R⁴ group | S | n | c | d |
|---|---|---|---|---|---|---|---|---|
| III-34 | 4 | —CH2CH3 | 4' | —CH2CH3 | — | 0 | 1 | 1 |
| III-35 | 4 | -t-Bu | 4' | -t-Bu | — | 0 | 1 | 1 |
| III-36 | 4 | —C10H21 | 4' | —C10H21 | — | 0 | 1 | 1 |
| III-37 | 4 | —OCH3 | 4' | —OCH3 | — | 0 | 1 | 1 |
| III-38 | 4 | —OCH2CH3 | 4' | —OCH2CH3 | — | 0 | 1 | 1 |
| III-39 | 4 | —N(CH3)2 | 4' | —N(CH3)2 | — | 0 | 1 | 1 |
| III-40 | 4 | —N(C4H9)2 | 4' | —N(C4H9)2 | — | 0 | 1 | 1 |
| III-41 | 4 | —CH2CH3 | 4' | —CH2CH3 | —SO2— | 1 | 1 | 1 |
| III-42 | 4 | -t-Bu | 4' | -t-Bu | —SO2— | 1 | 1 | 1 |
| III-43 | 4 | —C10H21 | 4' | —C10H21 | —SO2— | 1 | 1 | 1 |
| III-44 | 4 | —OCH2CH3 | 4' | —OCH2CH3 | —SO2— | 1 | 1 | 1 |
| III-45 | 4 | —N(CH3)2 | 4' | —N(CH3)2 | —SO2— | 1 | 1 | 1 |
| III-46 | 4 | H | 4' | H | —NH— | 1 | 1 | 1 |
| III-47 | 4 | H | 4' | H | —NC2H5— | 1 | 1 | 1 |
| III-48 | 4 | —CH2CH3 | 4' | —CH2CH3 | —NC2H5— | 1 | 1 | 1 |
| III-49 | 4 | —OMe | 4' | —OMe | —NC2H5— | 1 | 1 | 1 |
| III-50 | 4 | H | 4' | H | —NC14H29— | 1 | 1 | 1 |
| III-51 | 4 | —CH2CH3 | 4' | —CH2CH3 | —NC14H29— | 1 | 1 | 1 |
| III-52 | 4 | —OMe | 4' | —OMe | —NC14H29— | 1 | 1 | 1 |
| III-53 | 4 | H | 4' | H | —PCH3— | 1 | 1 | 1 |
| III-54 | 4 | —CH2CH3 | 4' | —CH2CH3 | —PCH3— | 1 | 1 | 1 |
| III-55 | 4 | —OMe | 4' | —OMe | —PCH3— | 1 | 1 | 1 |
| III-56 | 4 | H | 4' | H | —S•H2— | 1 | 1 | 1 |
| III-57 | 4 | H | 4' | H | —Si(CH3)2— | 1 | 1 | 1 |
| III-58 | 4 | —CH2CH3 | 4' | —CH2CH3 | —Si(CH3)2— | 1 | 1 | 1 |
| III-59 | 4 | —OMe | 4' | —OMe | —Si(CH3)2— | 1 | 1 | 1 |
| III-60 | 4 | H | 4' | H | —SiPh2— | 1 | 1 | 1 |
| III-61 | 4 | —CH2CH3 | 4' | —CH2CH3 | —SiPh2— | 1 | 1 | 1 |
| III-62 | 4 | —OMe | 4' | —OMe | —SiPh2— | 1 | 1 | 1 |

(In each pyridine ring, a nitrogen atom is at the 1-position and a carbon atom bound to B is at the 2-position.)

The complex compound (I) of the invention may be obtained by coordinating the ligands represented by the above formulas (II) and (III) to a metal atom.

Furthermore, the complex compound (I) of the invention has a structure in which a central atom is a metal atom, one of the ligands is represented by the formula (II), and another the ligands is represented by the formula (III).

In the complex compound (I), coligands may be coordinated thereto in addition to the ligands represented by the formulas (II) and (III). Examples of the coligand include isothiocyanate (—N=C=S) (hereinafter referred to as "NCS" at times), thiocyanate (—S—C≡N) (hereinafter referred to as "SCN" at times), diketonato, chloro, bromo, iodo, cyano, and a hydroxyl group, preferably NCS, and SCN.

A method for producing the complex compound (I) in which the central metal atom is Ru will be described. Examples of the method include a process in which [RuCl₂(p-cymene)]₂ is dissolved in an aprotic polar solvent such as N,N-dimethylformamide, bidentate and tridentate ligands are mixed therewith at about 40° to 180° C., if necessary salt providing the coligand is mixed therewith, and the resulting reaction solution is purified by means of recrystallization, chromatography, or the like.

Incidentally, as the Ru reagent, a divalent or trivalent Ru reagent is used. Examples of Ru reagent include RuCl₃ and RuCl₂(DMSO)₄.

Examples of the complex compound (I) include compounds represented by the following formula and shown in Table 3 (I-1 to I-50), compounds represented by the following formula and shown in Table 4 (I-51 to I-100), and compounds represented by the following formula and shown in Table 5 (I-101 to I-149).

TABLE 3

(I-1~I-149)

| Compound | M | L₁ | L₂ | X₁ = X₂ |
|---|---|---|---|---|
| I-1 | Ru | II-4 | III-2 | —NCS |
| I-2 | Ru | II-4 | III-3 | —NCS |
| I-3 | Ru | II-4 | III-8 | —NCS |

TABLE 3-continued $$\begin{array}{c}\text{(I-1~I-149)}\\ L_1 \left\{ (R^1-Y)_a \underset{N}{\overset{(A)_m}{\bigcirc}} \underset{N}{\overset{(Y-R^2)_b}{\bigcirc}} \right. \\ \left. \underset{(R^3)_c}{\overset{}{\bigcirc}} \underset{N}{\overset{M}{\underset{X_2}{\bigvee}}} \underset{X_1}{\overset{}{\underset{(R^4)_d}{\bigcirc}}} \right\} L_2 \end{array}$$

| Compound | M | L₁ | L₂ | X₁ = X₂ |
|---|---|---|---|---|
| I-4 | Ru | II-4 | III-9 | —NCS |
| I-5 | Ru | II-4 | III-11 | —NCS |
| I-6 | Ru | II-4 | III-12 | —NCS |
| I-7 | Ru | II-4 | III-17 | —NCS |
| I-8 | Ru | II-4 | III-18 | —NCS |
| I-9 | Ru | II-4 | III-21 | —NCS |
| I-10 | Ru | II-4 | III-23 | —NCS |
| I-11 | Ru | II-4 | III-25 | —NCS |
| I-12 | Ru | II-4 | III-28 | —NCS |
| I-13 | Ru | II-4 | III-30 | —NCS |
| I-14 | Ru | II-4 | III-31 | —NCS |
| I-15 | Ru | II-4 | III-32 | —NCS |
| I-16 | Ru | II-4 | III-36 | —NCS |
| I-17 | Ru | II-4 | III-37 | —NCS |
| I-18 | Ru | II-4 | III-40 | —NCS |
| I-19 | Ru | II-4 | III-50 | —NCS |
| I-20 | Ru | II-4 | III-51 | —NCS |
| I-21 | Ru | II-4 | III-52 | —NCS |
| I-22 | Ru | II-4 | III-53 | —NCS |
| I-23 | Ru | II-4 | III-57 | —NCS |
| I-24 | Ru | II-4 | III-59 | —NCS |
| I-25 | Ru | II-4 | III-60 | —NCS |
| I-26 | Ru | II-4 | III-62 | —NCS |
| I-27 | Ru | II-5 | III-2 | —NCS |
| I-28 | Ru | II-5 | III-3 | —NCS |
| I-29 | Ru | II-5 | III-9 | —NCS |
| I-30 | Ru | II-5 | III-12 | —NCS |
| I-31 | Ru | II-5 | III-17 | —NCS |
| I-32 | Ru | II-5 | III-18 | —NCS |
| I-33 | Ru | II-5 | III-21 | —NCS |
| I-34 | Ru | II-5 | III-24 | —NCS |
| I-35 | Ru | II-5 | III-25 | —NCS |
| I-36 | Ru | II-5 | III-28 | —NCS |
| I-37 | Ru | II-5 | III-30 | —NCS |
| I-38 | Ru | II-5 | III-31 | —NCS |
| I-39 | Ru | II-5 | III-37 | —NCS |
| I-40 | Ru | II-5 | III-40 | —NCS |
| I-41 | Ru | II-5 | III-50 | —NCS |
| I-42 | Ru | II-5 | III-51 | —NCS |
| I-43 | Ru | II-5 | III-52 | —NCS |
| I-44 | Ru | II-5 | III-53 | —NCS |
| I-45 | Ru | II-5 | III-57 | —NCS |
| I-46 | Ru | II-5 | III-59 | —NCS |
| I-47 | Ru | II-5 | III-60 | —NCS |
| I-48 | Ru | II-5 | III-62 | —NCS |
| I-49 | Ru | II-8 | III-3 | —NCS |
| I-50 | Ru | II-8 | III-9 | —NCS |

TABLE 4

| Compound | M | L₁ | L₂ | X₁ = X₂ |
|---|---|---|---|---|
| I-51 | Ru | II-8 | III-12 | —NCS |
| I-52 | Ru | II-8 | III-17 | —NCS |
| I-53 | Ru | II-8 | III-18 | —NCS |
| I-54 | Ru | II-8 | III-21 | —NCS |
| I-55 | Ru | II-8 | III-24 | —NCS |
| I-56 | Ru | II-8 | III-25 | —NCS |
| I-57 | Ru | II-8 | III-28 | —NCS |
| I-58 | Ru | II-8 | III-30 | —NCS |
| I-59 | Ru | II-8 | III-31 | —NCS |
| I-60 | Ru | II-8 | III-37 | —NCS |
| I-61 | Ru | II-8 | III-50 | —NCS |
| I-62 | Ru | II-9 | III-3 | —NCS |
| I-63 | Ru | II-9 | III-7 | —NCS |
| I-64 | Ru | II-9 | III-9 | —NCS |
| I-65 | Ru | II-9 | III-12 | —NCS |
| I-66 | Ru | II-9 | III-17 | —NCS |
| I-67 | Ru | II-9 | III-18 | —NCS |
| I-68 | Ru | II-9 | III-21 | —NCS |
| I-69 | Ru | II-9 | III-24 | —NCS |
| I-70 | Ru | II-9 | III-25 | —NCS |
| I-71 | Ru | II-9 | III-28 | —NCS |
| I-72 | Ru | II-9 | III-30 | —NCS |
| I-73 | Ru | II-9 | III-31 | —NCS |
| I-74 | Ru | II-13 | III-3 | —NCS |
| I-75 | Ru | II-13 | III-7 | —NCS |
| I-76 | Ru | II-13 | III-9 | —NCS |
| I-77 | Ru | II-13 | III-12 | —NCS |
| I-78 | Ru | II-13 | III-17 | —NCS |
| I-79 | Ru | II-13 | III-18 | —NCS |
| I-80 | Ru | II-13 | III-21 | —NCS |
| I-81 | Ru | II-13 | III-24 | —NCS |
| I-81 | Ru | II-13 | III-28 | —NCS |
| I-82 | Ru | II-13 | III-30 | —NCS |
| I-83 | Ru | II-13 | III-31 | —NCS |
| I-84 | Ru | II-4 | III-2 | —SCN |
| I-85 | Ru | II-4 | III-3 | —SCN |
| I-86 | Ru | II-4 | III-7 | —SCN |
| I-87 | Ru | II-4 | III-9 | —SCN |
| I-88 | Ru | II-4 | III-11 | —SCN |
| I-89 | Ru | II-4 | III-12 | —SCN |
| I-90 | Ru | II-4 | III-17 | —SCN |
| I-91 | Ru | II-4 | III-18 | —SCN |
| I-92 | Ru | II-4 | III-21 | —SCN |
| I-93 | Ru | II-4 | III-23 | —SCN |
| I-94 | Ru | II-4 | III-25 | —SCN |
| I-95 | Ru | II-4 | III-28 | —SCN |
| I-96 | Ru | II-4 | III-30 | —SCN |
| I-97 | Ru | II-4 | III-31 | —SCN |
| I-98 | Ru | II-4 | III-37 | —SCN |
| I-99 | Ru | II-4 | III-40 | —SCN |
| I-100 | Ru | II-4 | III-50 | —SCN |

TABLE 5

| Compound | M | L₁ | L₂ | X₁ = X₂ |
|---|---|---|---|---|
| I-101 | Ru | II-4 | III-51 | —SCN |
| I-102 | Ru | II-4 | III-52 | —SCN |
| I-103 | Ru | II-4 | III-53 | —SCN |
| I-104 | Ru | II-4 | III-57 | —SCN |
| I-105 | Ru | II-4 | III-59 | —SCN |
| I-106 | Ru | II-4 | III-60 | —SCN |
| I-107 | Ru | II-4 | III-62 | —SCN |
| I-108 | Ru | II-4 | III-2 | —CN |
| I-109 | Ru | II-4 | III-3 | —CN |
| I-110 | Ru | II-4 | III-7 | —CN |
| I-111 | Ru | II-4 | III-9 | —CN |
| I-112 | Ru | II-4 | III-11 | —CN |
| I-113 | Ru | II-4 | III-12 | —CN |
| I-114 | Ru | II-4 | III-17 | —CN |
| I-115 | Ru | II-4 | III-18 | —CN |
| I-116 | Ru | II-4 | III-21 | —CN |
| I-117 | Ru | II-4 | III-23 | —CN |
| I-118 | Ru | II-4 | III-25 | —CN |
| I-119 | Ru | II-4 | III-28 | —CN |
| I-120 | Ru | II-4 | III-30 | —CN |
| I-121 | Ru | II-4 | III-31 | —CN |
| I-122 | Ru | II-4 | III-2 | —Cl |

TABLE 5-continued

| Compound | M | $L_1$ | $L_2$ | $X_1 = X_2$ |
|---|---|---|---|---|
| I-123 | Ru | II-4 | III-3 | —Cl |
| I-124 | Ru | II-4 | III-7 | —Cl |
| I-125 | Ru | II-4 | III-9 | —Cl |
| I-126 | Ru | II-4 | III-11 | —Cl |
| I-127 | Ru | II-4 | III-12 | —Cl |
| I-128 | Ru | II-4 | III-17 | —Cl |
| I-129 | Ru | II-4 | III-18 | —Cl |
| I-130 | Ru | II-4 | III-21 | —Cl |
| I-131 | Ru | II-4 | III-23 | —Cl |
| I-132 | Ru | II-4 | III-25 | —Cl |
| I-133 | Ru | II-4 | III-28 | —Cl |
| I-134 | Ru | II-4 | III-30 | —Cl |
| I-135 | Ru | II-4 | III-31 | —Cl |
| I-136 | Os | II-4 | III-2 | —NCS |
| I-137 | Os | II-4 | III-3 | —NCS |
| I-138 | Os | II-4 | III-7 | —NCS |
| I-139 | Os | II-4 | III-9 | —NCS |
| I-140 | Os | II-4 | III-11 | —NCS |
| I-141 | Os | II-4 | III-12 | —NCS |
| I-142 | Os | II-4 | III-17 | —NCS |
| I-143 | Os | II-4 | III-18 | —NCS |
| I-144 | Os | II-4 | III-21 | —NCS |
| I-145 | Os | II-4 | III-23 | —NCS |
| I-146 | Os | II-4 | III-25 | —NCS |
| I-147 | Os | II-4 | III-28 | —NCS |
| I-148 | Os | II-4 | III-30 | —NCS |
| I-149 | Os | II-4 | III-31 | —NCS |

It is preferable that in the complex compound (I) $R^1$—$Y^1$ and $R^2$—$Y^2$ are each a group represented by the following formula (V'), $R^3$ and $R^4$ are each a hydrogen atom or at least one group selected from the group consisting of $C_1$-$C_{20}$ alkyl group, $C_1$-$C_{20}$ alkoxy group, $C_2$-$C_{20}$ alkoxyalkyl group, $C_6$-$C_{20}$ aryloxy group, $C_7$-$C_{20}$ arylalkyloxy group, and $C_7$-$C_{20}$ aryloxyalkyl group, and B is —S—.

(V')

A photosensitizing dye of the invention includes the complex compound (I) of the invention. The dye includes complex compound (I) alone, mixture of different complex compounds (I), and mixture of complex compound (I) and other dye different from the complex compound (I).

Examples of the dye which may be mixed with the complex compound (I) include a metal complex and an organic dye which absorb light with a wavelength of about 300 to 700 nm.

Examples of the metal complex which may be mixed therewith include metallophthalocyanines such as copper phthalocyanine and titanyl phthalocyanine, chlorophyll, hemin, and a ruthenium complex, osmium complex, iron complex, and zinc complex described in JP-A No. 1-220380 and JP-B No. 5-504023.

Examples of the ruthenium complex include: cis-bis(isothiocyanate)bis(2,2'-bipyridyl-4,4'-dicarboxylate)-ruthenium (II) bis-tetrabutylammonium; cis-bis(isothiocyanate)bis(2,2'-bipyridyl-4,4'-dicarboxylate)-ruthenium (II); tris(isothiocyanate)-ruthenium (II)-2,2':6',2"-terpyridine-4,4',4"-tricarboxylic acid tris-tetrabutylammonium; and cis-bis(isothiocyanate)(2,2'-bipyridyl-4,4'-dicarboxylate)(2,2'-bipyridyl-4,4'-dinonyl) ruthenium (II).

The organic dye is for example metal-free phthalocyanine, cyanine dye, merocyanine-based dye, xanthene-based dye, triphenylmethane dye, indoline-based organic dye, and squalilium-based dye.

Examples of the cyanine dye include NK1194 and NK3422 (which are produced by Nippon photosensitive dye Laboratories Inc.).

Examples of the merocyanine-based dye include NK2426 and NK2501 (which are produced by Nippon photosensitive dye Laboratories Inc.).

Examples of xanthene-based dye include uranin, eosin, rose bengal, rhodamine B, and dibromfluorescein.

Examples of triphenylmethane dye include malachite green and crystal violet.

Examples of coumarin-based dye include compound having the following structural unit such as NKX-2677 (produced by Hayashibara Biochemical Laboratories In.).

Examples of Indoline-based organic dye include compound having the following structural unit.

Examples of squalilium-based dye include compound having the following structural unit.

(coumarin-based dye)

(indoline-based dye)

(squalilium-based dye)

A photoelectric converter of the invention is a device including a semiconductor fine-particle layer on which a photosensitizing dye including the complex compound (I) of the invention is adsorbed, and a conductive substrate. The photosensitizing dye adsorbed thereon absorb even light energy with a long wavelength above 700 nm.

The photoelectric converter may be used as, for example, a photosensor sensing light with a wavelength of 700 nm or more which is absorbed by the photosensitizing die including the complex compound (I) of the invention, or photoelectrochemical cell described below.

The semiconductor fine particles used in the photoelectric converter of the invention has a primary particle diameter of usually about 1 to 5000 nm, preferably about 5 to 300 nm. The photoelectric converter may include other semiconductor particles having a primary particle diameter different from the semiconductor fine particles from the viewpoint of enhancing photoelectric conversion efficiency through the reflection of light. Furthermore, the semiconductor fine particles may be in tubular or hollow shape.

The semiconductor fine particles include, for example, metal oxide such as titanium oxide, tin oxide, zinc oxide, iron oxide, tungsten oxide, zirconium oxide, hafnium oxide, strontium oxide, indium oxide, cerium oxide, yttrium oxide, lanthanum oxide, vanadium oxide, niobium oxide, tantalum oxide, gallium oxide, nickel oxide, strontium titanate, barium titanate, potassium niobate, and sodium tantalate;

metallic halide such as silver iodide, silver bromide, copper iodide, and copper bromide;

metallic sulfide such as zinc sulfide, titanium sulfide, indium sulfide, bismuth sulfide, cadmium sulfide, zirconium sulfide, tantalum sulfide, molybdenum sulfide, silver sulfide, copper sulfide, tin sulfide, tungsten sulfide, and antimony sulfide;

metallic selenide such as cadmium selenide, zirconium selenide, zinc selenide, titanium selenide, indium selenide, tungsten selenide, molybdenum selenide, bismuth selenide, and lead selenide;

metallic telluride such as cadmium telluride, tungsten telluride, molybdenum telluride, zinc telluride, and bismuth telluride;

metallic phosphide such as zinc phosphide, gallium phosphide, indium phosphide, and cadmium phosphide;

gallium arsenide, a copper-indium-selenide, a copper-indium-sulfide, silicon, and germanium.

In addition, the semiconductor fine particles may be made of mixture thereof such as mixture of zinc oxide and tin oxide or mixture of tin oxide and titanium oxide.

The semiconductor fine particles include preferably metallic oxide such as titanium oxide, tin oxide, zinc oxide, iron oxide, tungsten oxide, zirconium oxide, hafnium oxide, strontium oxide, indium oxide, cerium oxide, yttrium oxide, lanthanum oxide, vanadium oxide, niobium oxide, tantalum oxide, gallium oxide, nickel oxide, strontium titanate, barium titanate, potassium niobate, sodium tantalate, mixture of zinc oxide and tin oxide, mixture of tin oxide and titanium oxide, more preferably titanium oxide from the viewpoint of relative low cost, availability and easy dyeing.

A conductive substrate used in the photoelectric converter of the invention (references 8 and 9 in FIG. 1) includes conductive substance alone or laminate of substrate and conductive substance.

Examples of the conductive substance include metal such as platinum, gold, silver, copper, aluminum, rhodium, indium, titanium, palladium, and iron; alloy thereof; conductive metallic oxide such as In—Sn multiple oxide and fluorine-doped tin oxide; carbon; and conductive polymer such as polyethylene dioxythiophene (PEDOT) and polyaniline.

The conductive polymer may be, for example, doped with a paratoluenesulfonic acid.

The conductive substrate has preferably a textured structure on its surface from viewpoint of confining and using incident light effectively.

Conductive layers (references 2 and 6 in FIG. 1) has preferably low resistance and high transparency (light transmittance of 80% at long wavelength of over 350 nm).

The conductive substrate (references to 8 and 9 in FIG. 1) is preferably prepared by coating conductive metallic oxide on glass or plastic substrate. The conductive substrate is more preferably conductive glass on which a fluorine-doped tin dioxide conductive layer is laminated. The plastic substrate include cyclic polyolefines (COP) such as ZEONOR (trademark, ZEON CORPORATION), APEL (trademark, MITSU CHEMICALS INC.), (trademark, TICONA Co., Ltd.), polyethylene terephthalate (PET), polyethylene naphthalate (PEN), poly(phenylene sulfide) (PPS), polycarbonate (PC), polypropylene (PP), polyimide (PI), triacetyl cellulose (TAC), syndiotactic polystyrene (SPS), polyallylate (PAR), poly(ethersulfone) (PES), poly(etherimide) (PEI), polysulfone (PSF), and polyamide (PA).

The conductive substrate include more preferably conductive PET on which an In—Sn complex oxide conductive layer is deposited from the viewpoint of low resistance and good transparency and easy availability.

Examples of method of forming the semiconductor fine-particle layer on the conductive substrate include a process of directly forming a thin film on the conductive substrate by spraying the semiconductor fine particles or the like, a process of electrically depositing a thin film of the semiconductor fine particles thereon by using the conductive substrate as an electrode, and a process of applying a slurry of the semiconductor fine particles on the conductive substrate and drying, hardening, or baking the slurry.

Examples of the method of applying the slurry of the semiconductor fine particles on the conductive substrate include doctor blading, sqeegeeing, spin coating, dip coating, screen printing and the like.

In these methods, the semiconductor fine particles has an average particle diameter of preferably from 0.01 to 100 μm in dispersed slurry.

Dispersion medium for the slurry is a medium which disperses the semiconductor fine particles. Examples thereof include water and organic solvents such as alcoholic solvents (ethanol, isopropanol, t-butanol, terpineol and so on) and ketones (acetone and so on). The water and organic solvents may be used in the form of mixtures. The dispersion medium may include polymer such as polyethylene glycol, surfactant such as Triton-X, organic or inorganic acid such as acetic acid, formic acid, nitric acid, or hydrochloric acid, and chelating agent such as acetylacetone.

The conductive substrate on which the slurry is applied is calcined. Calcination temperature is lower than a melting point (or the softening point) of substance such as the thermoplastic resin. An upper limit of the calcination temperature is usually 900° C., preferably 600° C. Calcination time is usually 10 hours or less. the semiconductor fine-particle layer on the conductive substrate has a thickness of usually from 1 to 200 μm, preferably from 5 to 50 μm.

Examples of method of forming the semiconductor fine-particle layer on the conductive substrate at relatively low temperature include a hydrothermal process in which a porous semiconductor fine-particle layer is formed by hydrothermal treatment (Hideki Minoura "Dye-Sensitized Photoelectrochemical Cell Intended For Practical Use", 2nd Chap., pp. 63 to 65, NTS 2003), an electrophoretic deposition process in which semiconductor particle-dispersed liquid is electrodeposited on a substrate (T. Miyasaka et al., Chem. Lett. 1250, 2002) and a press process in which a semiconductor paste applied on a substrate is dried and the resultant is pressed (Takehiko Yorozu "Dye-Sensitized Photoelectrochemical Cell Intended For Practical Use", 12th Chap., pp. 312 and 313, NTS 2003).

The surface of the semiconductor fine particle layer may be chemically plated with titanium tetrachloride aqueous solution or electrochemically plated with titanium trichloride aqueous solution. By plating, the surface area of the semiconductor fine particles is increased, the purity of the vicinities of the semiconductor fine particles is heightened, impurities such as iron on the surface of the semiconductor fine particles is covered up therewith, or the linkage and bond between the semiconductor fine particles is improved.

The semiconductor fine particles have preferably a large surface area so as to adsorb the dye for the photoelectric converter in large amounts. The surface area in the state in which the semiconductor fine particle layer is formed on the substrate is preferably more than 10 times as large as their projected area, more preferably more than 100 times as large as that area. An upper limit to the surface area is usually about 1000 times.

The semiconductor fine particle layer may include monolayer containing semiconductor fine particles or multilayer containing semiconductor fine particles and other semiconductor particles with different particle diameter from the semiconductor fine particles.

Examples of method of adsorbing the photosensitizing dye of the invention on the semiconductor fine particles include a process of dipping dried semiconductor fine particles in the photosensitizing dye solution for about 1 minute to about 24 hours. The adsorption of the photosensitizing dye may be performed at ambient temperature, or may be performed under reflux at elevated temperature. The adsorption of the photosensitizing dye may be performed before the application of the semiconductor fine particles, or may be performed after application; although the semiconductor fine particles and the photosensitizing dye may be simultaneously applied thereon such that the dye is adsorbed on the particles. It is more preferable that the photosensitizing dye is adsorbed on the semiconductor fine particle film after application. In the case that the semiconductor fine particle layer is heat-treated, the adsorption of photosensitizing dye is preferably performed after the heat treatment, more preferably performed rapidly before water adsorbs on the surface of the fine particle layer after the heat treatment.

It is preferable that non-adhered photosensitizing dye which is not adhered to the semiconductor fine particles is removed by cleaning to prevent decrease in the photosensitization effect caused by suspension of the non-adhered photosensitizing dye.

The photosensitizing dye to be adsorbed thereon may be used alone or in combination. In the case that the dye is used in a photoelectrochemical cell, it is preferable that the photosensitizing dye to be mixed together is selected such that a wavelength region, with which incident light such as sunlight is photoelectrically converted, is broadened as much as possible. In addition, the amount of the photosensitizing dye adsorbed on the semiconductor fine particles is preferably 0.01 to 1 m mole per gram of the semiconductor fine particles. It is preferable that the amount of the dye be fixed in such a manner because the photosensitization effect on the semiconductor fine particles is sufficiently obtained and there is a tendency to prevent decrease in photosensitization effect caused by suspension of the photosensitizing dye not adhering to the semiconductor fine particles.

To prevent an interaction, such as association and aggregation, between the photosensitizing dyes, a colorless compound may be coadsorbed. Examples of coadsorbed hydrophobic compound include steroid compounds with a carboxyl group (e.g., chenodeoxycholic acid). In addition, to promote removal of the extra photosensitizing dye, the semiconductor fine particles may be surface-treated using amine after the adsorption of the photosensitizing dye. Examples of the amine include preferably pyridine, 4-tert-butyl pyridine, and polyvinyl pyridine. In the case of liquid, these may be used as they are; in the case of solid, these may be used after dissolving in an organic solvent.

A photoelectrochemical cell of the invention includes the photoelectric converter, charge transport layer, and counter electrode and is capable of converting light into electricity. Photoelectrochemical cells includes the photoelectric converter, charge transport layer, and counter electrode in this order, and the conductive substrate of the photoelectric converter is electrically connected with the counter electrode. Electrical charge transfers between them, whereby electric power is generated.

Examples of other type of photoelectrochemical cell include a photoelectrochemical cell with a counter electrode and plural laminate including photoelectric converter and charge transport layer; and a photoelectrochemical cell with laminate including plural photoelectric converters, charge transport layer, and counter electrode.

Photoelectrochemical cells are broadly divided into wet photoelectrochemical cells and dry photoelectrochemical cells. In wet photoelectrochemical cells, a charge transport layer is formed using an electrolytic solution, and usually the charge transport layer between photoelectric converter and counter electrode is filled with electrolyte.

Examples of dry photoelectrochemical cells include a cell in which a charge transport layer between a photoelectric converter and a counter electrode is made of solid hole transport material.

Figure 1:
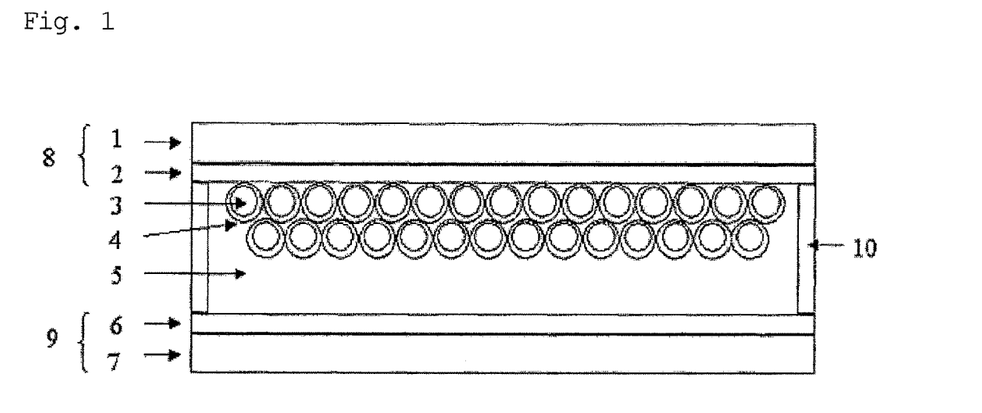
FIG. 1 is a schematic cross-sectional view of a photoelectrochemical cell of the present invention.

An embodiment of the photoelectrochemical cell of the invention is illustrated in FIG. 1. The cell includes a conductive substrate 8, a counter electrode 9 opposite to the conductive substrate 8, and a semiconductor fine-particle layer 3 which is between them and on which a dye 4 for a photoelectric converter is adsorbed. In the case that the photoelectric converter is of wet type, the semiconductor fine particle layer 3 is filled with electrolyte 5 and is sealed with sealant 10.

The conductive substrate 8 includes a substrate 1 and a conductive layer 2 in turn from above. The counter electrode 9 includes a substrate 7 and a conductive layer 6 in turn from below.

In the case that the photoelectrochemical cell of the invention is of wet type. Examples of electrolyte for the electrolytic solution in the charge transport layer include combination of $I_2$ and various iodides, combination of $Br_2$ and various bromides, combination of salt of ferrocyanic acid and metal complex of salt of ferricyanic acid, combination of ferrocene and metal complex of ferricinium ion, combination of alkylthiol and sulfur compounds of alkyldisulfide, combination of alkylviologen and reduced form thereof, and combination of polyhydroxy-benzenes and oxidized form thereof.

Examples of the iodide combined with $I_2$ include: metallic iodides such as LiI, NaI, KI, CsI, and $CaI_2$; iodine salts of tetravalent imidazolium compounds such as 1-propyl-3-methylimidazolium iodide and 1-propyl-2,3-dimethylimidazolium iodide; iodine salts of tetravalent pyridinium compounds; and iodine salts of tetraalkylammonium compounds.

Examples of the bromide combined with $Br_2$ include: metallic bromides such as LiBr, NaBr, KBr, CsBr, and $CaBr_2$; and bromine salts of tetravalent ammonium compounds such as tetraalkylammonium bromide and pyridinium bromide.

Examples of alkylviologen include methylviologen chloride, hexylviologen bromide, and benzylviologen tetrafluoroborate. Examples of polyhydroxy-benzenes include hydroquinone and naphthohydroquinone.

It is preferable that the electrolyte is a combination of $I_2$ and at least one iodide selected from the group consisting of metallic iodide, iodine salt of tetravalent imidazolium compound, iodine salt of tetravalent pyridinium compound, and iodine salt of tetraalkylammonium compound.

Examples of an organic solvent for the electrolytic solution includes: nitrile-based solvent such as acetonitrile, methoxyacetonitrile, and propionitrile; carbonate-based solvent such as ethylene carbonate and propylene carbonate; 1-methyl-3-propylimidazolium iodide and 1-methyl-3-hexylimidazolium iodide; ionic liquid such as 1-ethyl-3-methylimidazolium-bis(trifluoromethane sulfonic acid)imide; lactone-based solvent such as γ-butyl lactone; and amide-based solvent such as N,N-dimethylformamide. These solvents may be gelled with polyacrylonitrile, polyvinylidene fluoride, poly 4-vinylpyridine, or a gelatinizer described in Chemistry Letters, 1241 (1998).

In the case that the photoelectrochemical cell of the invention is of dry type, examples of solid hole transport material for the formation of the charge transport layer include: p-type inorganic semiconductor including monovalent copper such as CuI and CuSCN; aromatic amine described in Synthetic Metal, 89,215 (1997) and Nature, 395,583 (1998); and conductive polymer such as polythiophene and derivatives thereof; polypyrrole and derivative thereof; polyaniline and derivative thereof; poly(p-phenylene) and derivative thereof; and poly(p-phenylenevinylene) and derivative thereof.

The counter electrode in the photoelectrochemical cell of the invention is electrically conductive; as the counter electrode, a substrate same as the conductive substrate may be used to maintain its strength and improve its sealing property.

In order for light to penetrate the semiconductor fine particle layer on which the dye for the photoelectric converter is adsorbed, at least one of the conductive substrate and the counter electrode is usually substantially transparent. In the photoelectric converter of the invention, it is preferable that the conductive substrate with the semiconductor fine particle layer is transparent and light irradiation is done from the conductive substrate side. In this case, it is more preferable that the counter electrode 9 is optically reflective.

The counter electrode 9 of the photoelectrochemical cell may include glass or plastic substrate on which metal, carbon, or conductive oxide is deposited. Typically, the conductive layer may be formed using a method such as vapor deposition or sputtering such that its thickness is 1 mm or less, preferably from 5 nm to 100 μm. According to the invention, it is preferable that the counter electrode include glass on which platinum or carbon is deposited, or that a conductive layer is formed by vapor deposition or sputtering.

To prevent leakage and vaporization of electrolyte in the photoelectrochemical cell, sealing may be done by using a sealant. Examples of the sealant include ionomer resin such as HIMILAN (produced by Du Pont-Mitsui Polychemicals Co., Ltd.), glass frit, hot-melt adhesive such as SX1170 (produced by Solaronix Inc.), adhesive such as Amosil 4 (produced by Solaronix Inc.), and BYNEL (produced by Du Pont).

The invention provides the compound (I) which is used in a photoelectric converter having high photoelectric conversion efficiency even at long wavelength of 700 nm or more. It is easy to produce the compound (I). The compound has high degree of solubility in the organic solvent, and is adsorbed on the semiconductor fine particles to a large extent, and therefore is suitably used in a photoelectric converter such as photoelectrochemical cell.

EXAMPLES

The present invention will be described below in further detail based on examples; however, it is needless to say that the invention is not limited to these examples.

Production Example 1

Production Example of Compound (I-2)

After the substitution of a nitrogen gas within a reaction vessel, [RuCl$_2$(p-cymene)]$_2$ (31 mg, 0.05 mmol) (produced by Kanto Chemical Co., Inc.) and N,N-dimethylformamide (20 ml) was charged thereinto, the mixture was stirred at ambient temperature, and then it was confirmed that the mixture was dissolved. Thereafter, the compound III-3 (prepared using a method described in Eur. J. Inorg. Chem., 1353 (2001)) (22 mg, 0.10 mmol) was charged therein, the mixture was stirred at ambient temperature for 18 hr, and then it was confirmed with HPLC that the materials disappeared. Then the compound II-4 (prepared using a method described in Monatsheftefuer Chemie (1988), 119(1), 1-15) (46 mg, 0.10 mmol) was charged thereinto, and then stirring was done for 5 hr at a temperature raised to 80° C. Thereafter, a solution made by dissolving potassium thiocyanate (101 mg, 1.03 mol) in water (2 ml) was charged thereinto, following which the mixture was stirred at 100° C. for 7 hr. The following is a $^1$H-NMR spectrum of the ester structure of the compound II-4.

(CDCl$_3$ BURKER DPX300)

After their reaction, the reaction solution was concentrated with an evaporator, the concentrate was suspended with water, and then the mixture was crystallized in a state in which the pH of the suspension was lowered to about 1 with 1N HCl. After its filtering, the obtained substance was sufficiently washed with water, giving a purple solid. Then the crystal was aliquoted by means of high performance liquid chromatography to give a purple solid of high purity. It was confirmed with ESI-MS that the resulting solid was the desired compound (I-2) (with a molecular weight of 922).

Compound (I-2)

ESI-MS (m/z), m/z=922 M$^f$

Example 1

On a surface of a piece of conductive glass with a fluorine-doped tin oxide film (from Nippon Sheet Glass Co., Ltd.—10Ω/□) as a conductive substrate, a Ti nanoxide T/SP (Trade Name) (from Solaronix) as a titanium-oxide dispersion liquid was applied with a screen printer, after which its baking was performed at 500° C. Then the glass was cooled to make a laminate of the conductive substrate and the semiconductor particle layer, following which the laminate was immersed in a solution (in which the compound (I-2) was contained at a concentration of 0.0003 mol/l and a solvent was ethanol) for 16 hr. After being taken out of the solution, the laminate was washed with acetonitrile and then air-dried, giving a laminate including the conductive substrate and the semiconductor fine-particle layer on which the photosensitizing dye had been adsorbed (the area of the titanium-oxide electrode was 24 mm$^2$). Next, a 25-µm-thick polyethylene terephthalate film was provided around the layer as a spacer. Thereafter, the layer was impregnated with an electrolytic solution (solvent: acetonitrile, concentration of iodine in solvent: 0.05 mol/l, lithium iodide concentration: 0.1 mol/l, 4-t-butylpyridine concentration: 0.5 mol/l, and 1-propyl-2,3-dimethylimidazolium iodide concentration: 0.6 mol/l). Finally, a piece of platinum-evaporated glass as a counter electrode was stacked thereon, giving a photoelectrochemical cell in which the conductive substrate, the semiconductor fine-particle layer on which the photosensitizing dye had been adsorbed, and the counter electrode (conductive substrate) had been stacked together and in which the electrolytic solution had been impregnated between the conductive substrate and the counter electrode. The IPCE (incident photon-to-current efficiency) of the photoelectrochemical cell thus fabricated was measured using an IPCE measuring apparatus (from Bunkoh Keiki Co., Ltd.).

The IPCE of the photoelectrochemical cell implemented in Example 1 was shown in Table 6.

Production Example 2

Production Example of Compound (I-4)

The same reaction, post-processing, and refinement as those described in Production Example 1 were conducted except that the compound (III-9) was used instead of the compound (III-3), giving the compound (I-4).

It was confirmed with ESI-MS that the resulting solid was the desired compound (I-4 with a molecular weight of 926).
Compound (I-4)
  ESI-MS (m/z)
  m/z=926 M$^f$
  m/z=868 deNCS Structure [M-NCS]$^+$

Example 2

The same processing as that described in Example 1 was conducted except that as a photosensitizing dye, the compound (I-4) was used instead of the compound (I-2), giving a photoelectrochemical cell. Then its IPCE was measured as in Example 1. The measurement result was shown in Table 6.

Production Example 3

Production Example of Compound (I-19)

The same reaction, post-processing, and refinement as those described in Production Example 1 were conducted except that the compound (III-50) was used instead of the compound (III-3), giving the compound (I-19).

It was confirmed with ESI-MS that the resulting solid was the desired compound (I-19 with a molecular weight of 1045).
Compound (I-19)
  ESI-MS (m/z)
  m/z=1045 M$^f$
  m/z=987 deNCS Structure [M-NCS]$^+$

Example 3

The same processing as that described in Example 1 was conducted except that as a photosensitizing dye, the compound (I-19) was used instead of the compound (I-2), giving a photoelectrochemical cell. Then its IPCE was measured as in Example 1. The measurement result was shown in Table 6.

Production Example 4

Production Example of Compound (I-17)

The same reaction, post-processing, and refinement as those described in Production Example 1 were conducted except that the compound (III-37) was used instead of the compound (III-3), giving the compound (I-17).

It was confirmed with ESI-MS that the resulting solid was the desired compound (I-17 with a molecular weight of 894).
Compound (I-17)
  ESI-MS (m/z)
  m/z=894 M$^f$
  m/z=836 deNCS Structure [M-NCS]

Example 4

The same processing as that described in Example 1 was conducted except that as a photosensitizing dye, the compound (I-17) was used instead of the compound (I-2), giving a photoelectrochemical cell. Then its IPCE was measured as in Example 1. The measurement result was shown in Table 6.

Example 5

The same processing as that described in Example 1 was conducted except that as a photosensitizing dye, the compound (I-4') in which a tetra n-butylammonium salt is formed at one side of carboxyl groups was used in stead of the compound (I-4), giving a photoelectrochemical cell. Then its IPCE was measured as in Example 1. The measurement result was shown in Table 6.

Comparative Example 1

The same processing as that described in Example 1 was conducted except that as a photosensitizing dye, cis-bis(isothiocyanate)bis(2,2'-bipyridyl-4,4'-dicarboxylate)-ruthenium (II) (the compound (I)) was used to give a photoelectrochemical cell. Then its IPCE was measured as in Example 1. The measurement result was shown in Table 6.

TABLE 6

| Compound | Example 1 (I-2) | Example 2 (I-4) | Example 3 (I-19) | Example 4 (I-17) | Example 5 (I-4') | Compar. Example 1 (1) |
|---|---|---|---|---|---|---|
| IPCE(700 nm) | 10.3% | 19.4% | 15.2% | 9.3% | 22.0% | 6.5% |
| IPCE(750 nm) | 2.7% | 6.2% | 5.5% | 2.7% | 8.6% | 1.6% |
| IPCE(800 nm) | 0.3% | 1.9% | 1.2% | 0.4% | 2.0% | 0.1% |

INDUSTRIAL APPLICABILITY

The complex compound (I) of the present invention has high photoelectric conversion efficiency at not only the visible light but the near-infrared and suitably used as a photosensitizing dye. The photoelectric converter is used as a solar cell under sunlight irradiation and a photoelectrochemical cell under artificial lights irradiation indoor or in a tunnel, since a photoelectric converter including the compound has high photoelectric conversion efficiency. Furthermore, the photoelectric converter is irradiated with light and electric current flows through the photoelectric converter.

The invention claimed is:

1. A complex compound (I) obtained by coordinating a ligand represented by the formula (II) and a ligand represented by the formula (III) to a metal atom, wherein $Y^1$ and $Y^2$ are each a group represented by the formula (IV), $R^1$ and $R^2$ each bind to Ar, Ar represents thiophene, p=1, $R^1$ and $R^2$ each independently represent a protogenic group or a salt thereof, at least one of $R^1$ and $R^2$ is a protogenic group, $R^3$ and $R^4$ each independently represent an aprotogenic group, $R^3$ and $R^4$ may be bound together, A and B each independently represent a group including an element of group 14, 15, or 16 of the Periodic Table, m and n each independently represent an integer of 0 to 2, a, b, c, and d each independently represent an integer of 0 to 2, and a+b≧1.

2. A complex compound (I) obtained by coordinating a ligand represented by the formula (II) and a ligand represented by the formula (III) to a metal atom, wherein $Y^1$ and $Y^2$ are each a group represented by the formula (IV), Ar represents thiophene and p=1, $R^1$ and $R^2$ each bind to Ar and each independently represent a protogenic group or a salt thereof, at least one of $R^1$ and $R^2$ is a protogenic group, $R^3$ and $R^4$ each independently represent an aprotogenic group, $R^3$ and $R^4$ may be bound together, A and B are each independently at least one group selected from the group consisting of —S—, —SO—, —SO$_2$—, —PR$^5$—, —NR$^5$ —Si(R$^5$) (R$^6$)—, and —Se—, and $R^5$ and $R^6$ each independently represent a hydrogen atom, $C_1$-$C_{20}$ alkyl group, or $C_6$-$C_{20}$ aryl group, m and n each independently represent an integer of 0 to 2, and m+n≧1, a, b, c, and d each independently represent an integer of 0 to 2, and a+b≧1.

3. A complex compound (I) obtained by coordinating a ligand represented by the formula (II) and a ligand represented by the formula (III) to a metal atom, wherein $R^1$—$Y^1$— and $R^2$—$Y^2$— are each a group represented by the formula (V'), (V')

$R^3$ and $R^4$ are each a hydrogen atom or at least one group selected from the group consisting of $C_1$-$C_{20}$ alkyl group, alkoxy group, $C_2$-$C_{20}$ alkoxyalkyl group, $C_6$-$C_{20}$ aryloxy group, $C_7$-$C_{20}$ arylalkyloxy group, and $C_7$-$C_{20}$ aryloxyalkyl group, A represents a group including an element of group 14, 15, or 16 of the Periodic Table, B is —S—, m represents an integer of 0 to 2, n represents an integer of 1 to 2, a, b, c, and d each independently represent an integer of 0 to 2, and a+b≧1.

4. A complex compound (I) obtained by coordinating a ligand represented by the formula (II) and a ligand represented by the formula (III) to a metal atom, wherein $R^3$ and $R^4$ are each a hydrogen atom or at least one group selected from the group consisting of $C_1$-$C_{20}$ alkyl group, $C_1$-$C_{20}$ alkoxy group, $C_2$-$C_{20}$ alkoxyalkyl group, $C_6$-$C_{20}$ aryloxy group, $C_7$-$C_{20}$ arylalkyloxy group, and $C_7$-$C_{20}$ aryloxyalkyl group, $R^3$ and $R^4$ may be bound together, A is at least one group selected from the group consisting of —S—, —SO—, —$SO_2$—, —$PR^5$—, —$NR^5$—, —Si($R^5$)($R^6$), and —Se—, B is —S—, $R^5$ and $R^6$ each independently represent a hydrogen atom, $C_1$-$C_{20}$ alkyl group, or $C_6$-$C_{20}$ aryl group, m represents an integer of 0 to 2, n represents an integer of 1 to 2, and m+n≧1, a, b, c, and d each independently represent an integer of 0 to 2, and a+b≧1, and $R^1$—$Y^1$— and $R^2$—$Y^2$— are each a group represented by the formula (V')

(V')

5. A complex compound (I) obtained by coordinating a ligand represented by the formula (II) and a ligand represented by the formula (III) to a metal atom, wherein $Y^1$ and $Y^2$ each independently represent a group including an unsaturated hydrocarbon group and an aromatic ring, $R^1$ and $R^2$ each independently represent a protogenic group or a salt thereof, at least one of $R^1$ and $R^2$ is a protogenic group, $R^3$ and $R^4$ each independently represent an aprotogenic group, $R^3$ and $R^4$ may be bound together, A and B are —S—, m and n each independently represent an integer of 1 to 2, and m+n≧2, a, b, c, and d each independently represent an integer of 0 to 2, and a+b≧1.

* * * * *